(12) United States Patent
Chao (10) Patent No.: US 7,988,652 B2
(45) Date of Patent: Aug. 2, 2011

(54) JOINT BRACE ADJUSTABLE DEVICE (75) Inventor: Chia-Chang Chao, Taipei (TW)

(73) Assignee: Huntex Corporation, Taipei (TW)

( * ) Notice: Subject to any disclaimer, the term of this patent is extended or adjusted under 35 U.S.C. 154(b) by 274 days.

(21) Appl. No.: 12/324,612

(22) Filed: Nov. 26, 2008

(65) Prior Publication Data
US 2010/0130899 A1 May 27, 2010

(51) Int. Cl.
*A61F 11/00* (2006.01)
*A61F 5/37* (2006.01)
*A61F 5/00* (2006.01)
*A61F 5/02* (2006.01)
*A41D 13/00* (2006.01)
*F16C 11/00* (2006.01)
*F16B 39/00* (2006.01)
*F16B 39/04* (2006.01)
*F16B 35/00* (2006.01)
*A41F 1/00* (2006.01)
*A44B 9/12* (2006.01)

(52) U.S. Cl. .............. 602/19; 128/868; 128/882; 602/5; 602/16; 602/20; 602/23; 602/26; 602/27; 602/36; 2/24; 2/44; 2/45; 403/92; 411/81; 411/87; 411/90; 411/393; 24/522; 24/542; 24/707.9

(58) Field of Classification Search .................. 128/868, 128/882; 602/5, 16, 19, 20, 23, 26, 27, 36; 2/24, 44, 45; 403/92; 411/81, 87, 90, 393; 24/522, 542, 707.9; 133/69, 75, 141, 142
See application file for complete search history.

(56) References Cited

U.S. PATENT DOCUMENTS
7,037,287 B2 * 5/2006 Cormier et al. ................. 602/23

FOREIGN PATENT DOCUMENTS
TW M311408 5/2007
TW M328862 3/2008
* cited by examiner

*Primary Examiner* — Patricia M Bianco
*Assistant Examiner* — Nihir Patel
(74) *Attorney, Agent, or Firm* — Muncy, Geissler, Olds & Lowe, PLLC (57) ABSTRACT

The present invention discloses a pivotal disc is pivotally coupled to a first brace and a second brace. The pivotal disc has a motion-limit member and a positioning member limiting the angle by which the second brace rotates with respect to the first brace with the pivotal disc being the axis and fixing the angle between the first and second braces. The present invention is characterized in that the motion-limit member uses a range-adjust member to push a slide block and determine the range that a block portion of the second brace is blocked by the slide block, and that the positioning member uses a switch knob actuates on end of a positioning rod to engage with or depart from a positioning notch on the pivotal disc, and that the pivotal disc has two limit elements to define the maximum movement range of the first brace and the second brace.

5 Claims, 10 Drawing Sheets

JOINT BRACE ADJUSTABLE DEVICE

FIELD OF THE INVENTION

The present invention relates to a joint brace adjustable device, particularly to a device to fix the angle of a joint or limit the movement of a joint.

BACKGROUND OF THE INVENTION

Joints are the pivots of our bodies, whereby we can perform various movements. Among them, the knee joints and the elbow joints are more heavily burdened and more likely to be hurt.

Thus, there are various joint braces invented. The joint braces may be categorized into the prophylactic braces preventing from joint hurts, the functional braces limiting joint movements after surgery, and the rehabilitative braces fixing the angle of a joint during rehabilitation. The abovementioned joint braces respectively have different structures to implement different functions. There are also multi-functional joint braces. For example, a Taiwan patent No. M311408 disclosed an "Adjusting Device for Knee Joint Fixer (1)", wherein the slide way thereof has insert slots, and two position-limiting blocks are used to fix the joint angle or limit joint movements. However, the structure is too complicated, and the operation process thereof is too troublesome. For example, suppose that the adjusting devices are applied to both knee joint, and that each leg needs two fixers; the user has to adjust eight position-limiting blocks respectively. There is also a Taiwan patent No. M328862 disclosing a "Positioning Mechanism for Knee Joint Fixer", which is based on the preceding patent, wherein an engaging element is displaced to engage with one end of the second plate and fix the position. The application thereof is only using the engaging element to fix the position of the second plate, but the cost thereof increases because the structure becomes further complicated.

SUMMARY OF THE INVENTION

One objective of the present invention is to provide a joint brace adjustable device, which adopts a distinct structure to replace the conventional complicated structure, and which is applied to fixing the joint angle and limiting the joint movement, and which can increase the adaptability of the joint brace fixer.

To achieve the abovementioned objective, the present invention proposes a joint brace adjustable device, which comprises a first brace, a second brace, and a pivotal disc fixedly coupled to one end of the first brace and pivotally coupled to one end of the second brace. The pivotal disc has a motion-limit member to define the range of the relative movement of the first brace and the second brace. The pivotal disc has a positioning slot, and the positioning slot has a plurality of positioning notches. The positioning notch cooperates with a positioning member to determine the angle between the first brace and the second brace. The present invention is characterized in that the motion-limit member includes a plurality of position-fix slots formed on the pivotal disc, a slide block arranged inside the position-fix slot, a range-adjust member, and a block portion formed on the second brace. An elastic element is arranged on one end of the slide block and pushes the slide block toward the axis of the pivotal disc. When the range-adjust member rotates with respect to the pivotal disc, it presses the slide block to move toward the circumference of the pivotal disc. When the slide block is pushed toward the axis of the pivotal disc, the slide block will block the block portion. When the slide block is moved toward the circumference of the pivotal disc, the block portion does not contact the slide block. The positioning member has a positioning rod and a switch knob coupled to the positioning rod. One end of the positioning rod matches the shape of the positioning notch. Switching the switch knob actuates the positioning rod to engage with or depart from the positioning notch. The pivotal disc has an upper disc and a lower disc; the first brace is fixedly coupled to between the upper disc and the lower disc; the second brace are pivotally coupled to between the upper disc and the lower disc. The pivotal disc has two limit elements to define the maximum movement range of the first brace and the second brace via blocking two lateral edges of the second brace.

Via the abovementioned structure, the present invention has the following advantages over the conventional technology:

1. Greatly simplifying the structure, effectively reduce the cost, and favoring mass-production;
2. Conveniencing the operation of fixing the angle of a joint via merely moving the positioning member to an intended angle and locking it when the motion-limit member is in an unlock state; and
3. Conveniencing the operation of limiting the movement range of a joint via merely moving the motion-limit member to an intended movement range and locking it when the positioning member is in an unlock state.

DETAILED DESCRIPTION OF THE PREFERRED EMBODIMENTS

Below are described in detail the technical contents of the present invention.

Firstly is described the relationship of the primary components. Refer to FIGS. 1-4. The joint brace adjustable device of the present invention comprises a first brace 10, a second brace 20, and a pivotal disc 30 connected with one end of the first brace 10 and pivotally coupled to one end of the second brace 20. The pivotal disc 30 has a motion-limit member 40 limiting the angle by which the second brace 20 rotates with respect to the first brace 10 with the pivotal disc 30 being the axis. The pivotal disc 30 has a positioning slot 60, and the positioning slot 60 has a plurality of positioning notches 61. The positioning notch 61 cooperates with a positioning member 51 to fix the second brace 20, and thus the first brace 10 and the second brace 20 contains a specified angle. The present invention is characterized in that the motion-limit member 40 has a plurality of position-fix slots 41 formed on the pivotal disc 30, a slide block 42 arranged inside the position-fix slot 41, a range-adjust member 43, and a block portion 44 formed on one end of the second brace 20. An elastic element 70 is arranged on one end of the slide block 42 and pushes the slide block 42 toward the axis of the pivotal disc 30. When the range-adjust member 43 rotates with respect to the pivotal disc 30, it presses the slide block 42 to move toward the circumference of the pivotal disc 30. When the slide block 42 is pushed toward the axis of the pivotal disc 30 during the rotation of the range-adjust member 43, the slide block 42 will block the block portion 44. When the slide block 42 is pressed and then moved toward the circumference of the pivotal disc 30 during the rotation of the range-adjust member 43, the block portion 44 does not contact the slide block 42. The positioning member 51 has a positioning rod 511 and a switch knob 512 coupled to the positioning rod 511. One end of the positioning rod 511 matches the shape of the positioning notch 61. Switching the switch knob 512 actuates the positioning rod 511 to engage with or depart from the positioning notch 61. The pivotal disc 30 has an upper disc 31 and a lower disc 32. The first brace 10 is fixedly coupled to between the upper disc 31 and the lower disc 32; the second brace 20 are pivotally coupled to between the upper disc 31 and the lower disc 32. The pivotal disc 30 has two limit elements 33. When the second brace 20 has a maximum rotational displacement with respect to the first brace 10, the limit element 33 will press the two lateral edges of the second brace 20 and stop the second brace 20. In the present invention, each of the positioning rod 511 and the slide block 42 are both connected with an elastic element 70. Hereinbefore has been described the relationship of the primary components for fixing the angle of a joint or limiting the movement range of a joint according to the present invention. Below are described the detailed operations thereof.

Figure 1:
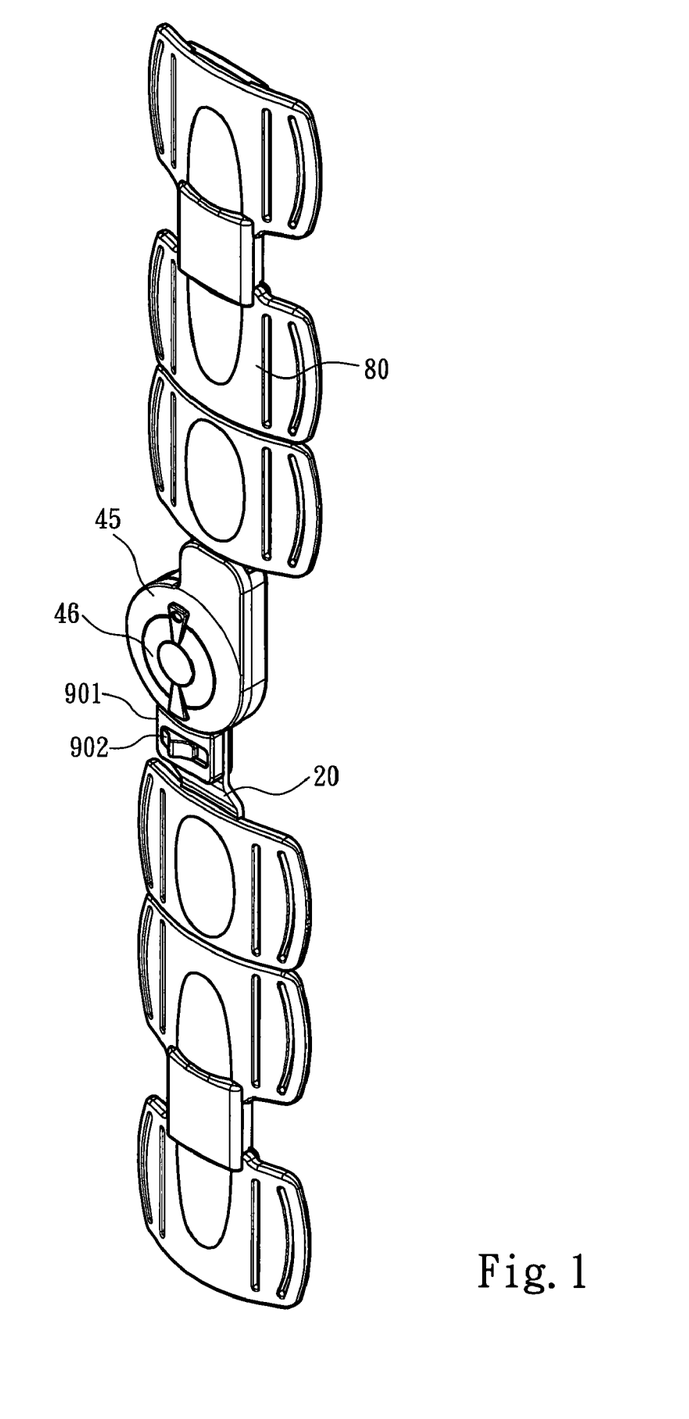
FIG. 1 is a perspective view of the appearance of a joint brace adjustable device according to the present invention.
Figure 2:
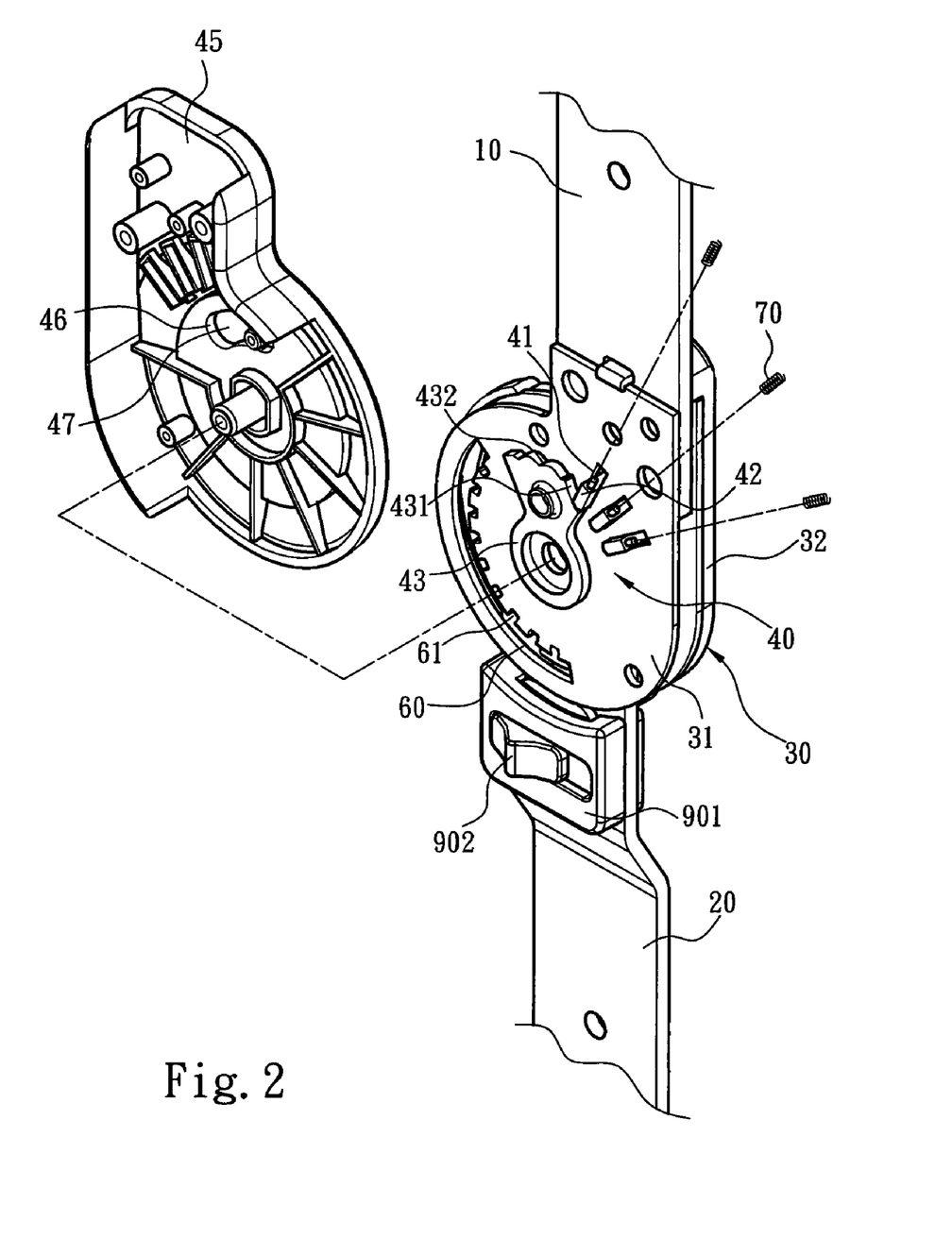
FIG. 2 is a brief exploded view of a joint brace adjustable device according to the present invention.
Figure 3:
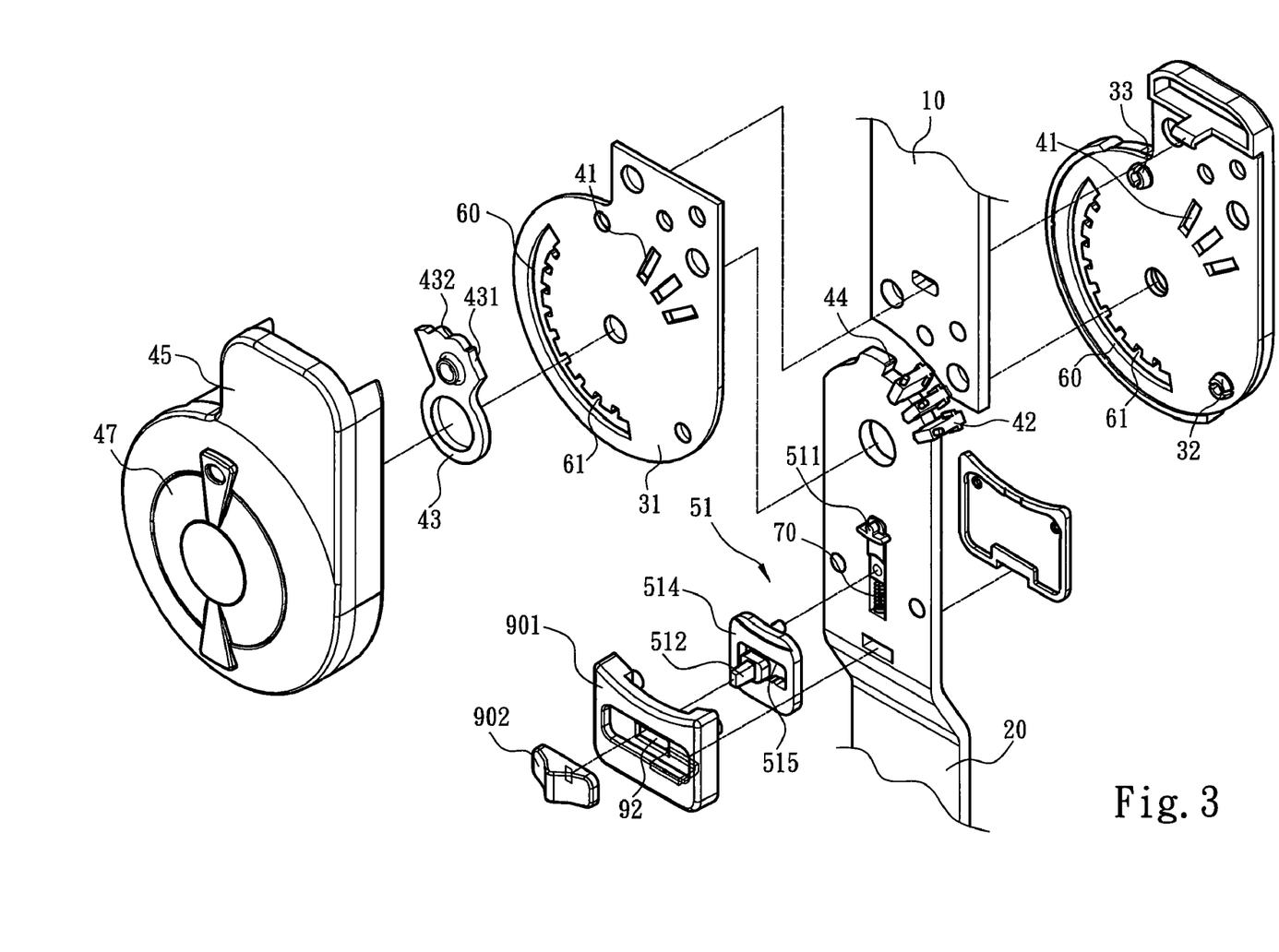
FIGS. 3 and 4 are detailed exploded views of a joint brace adjustable device according to the present invention.
Figure 4:
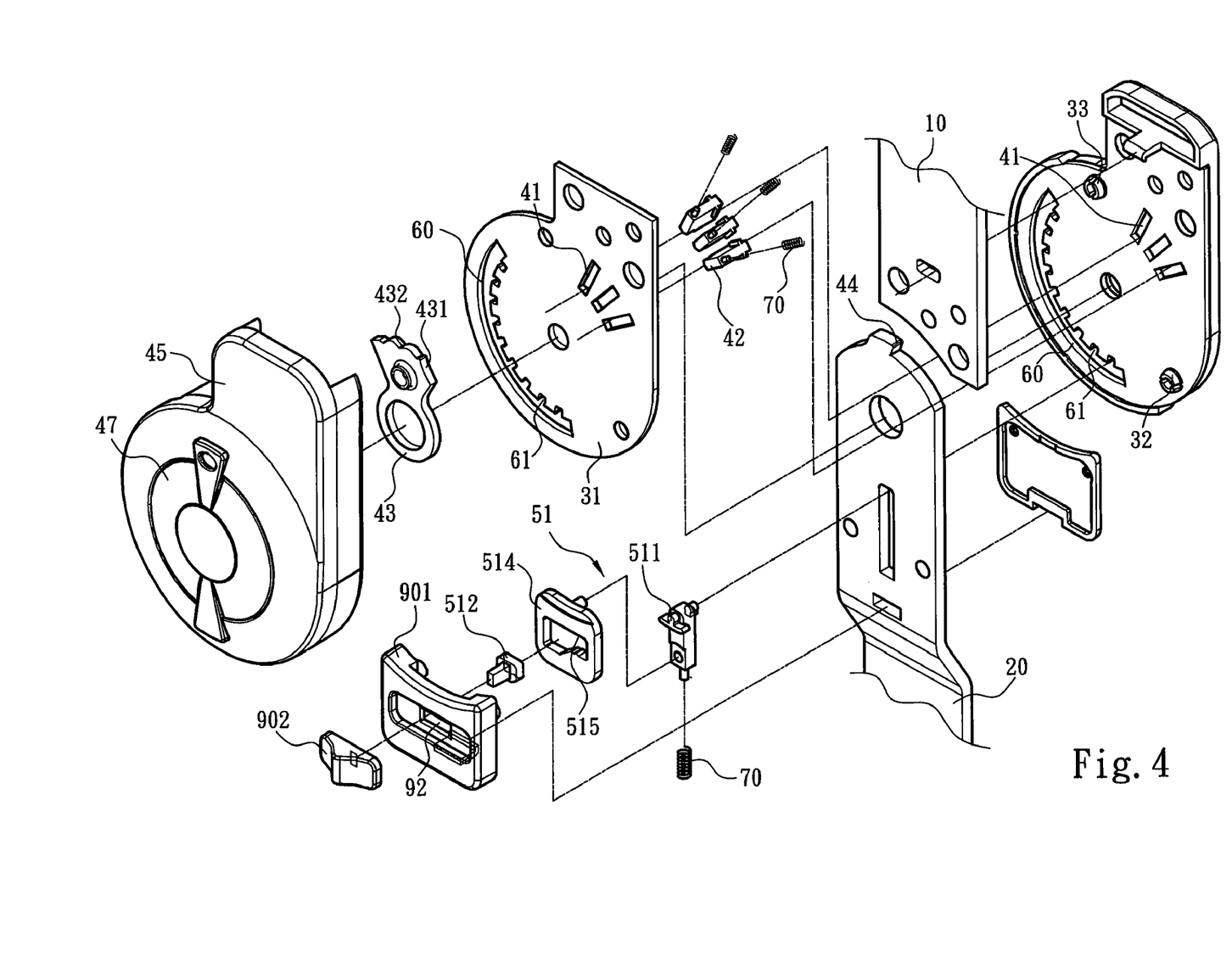
Figure 5:
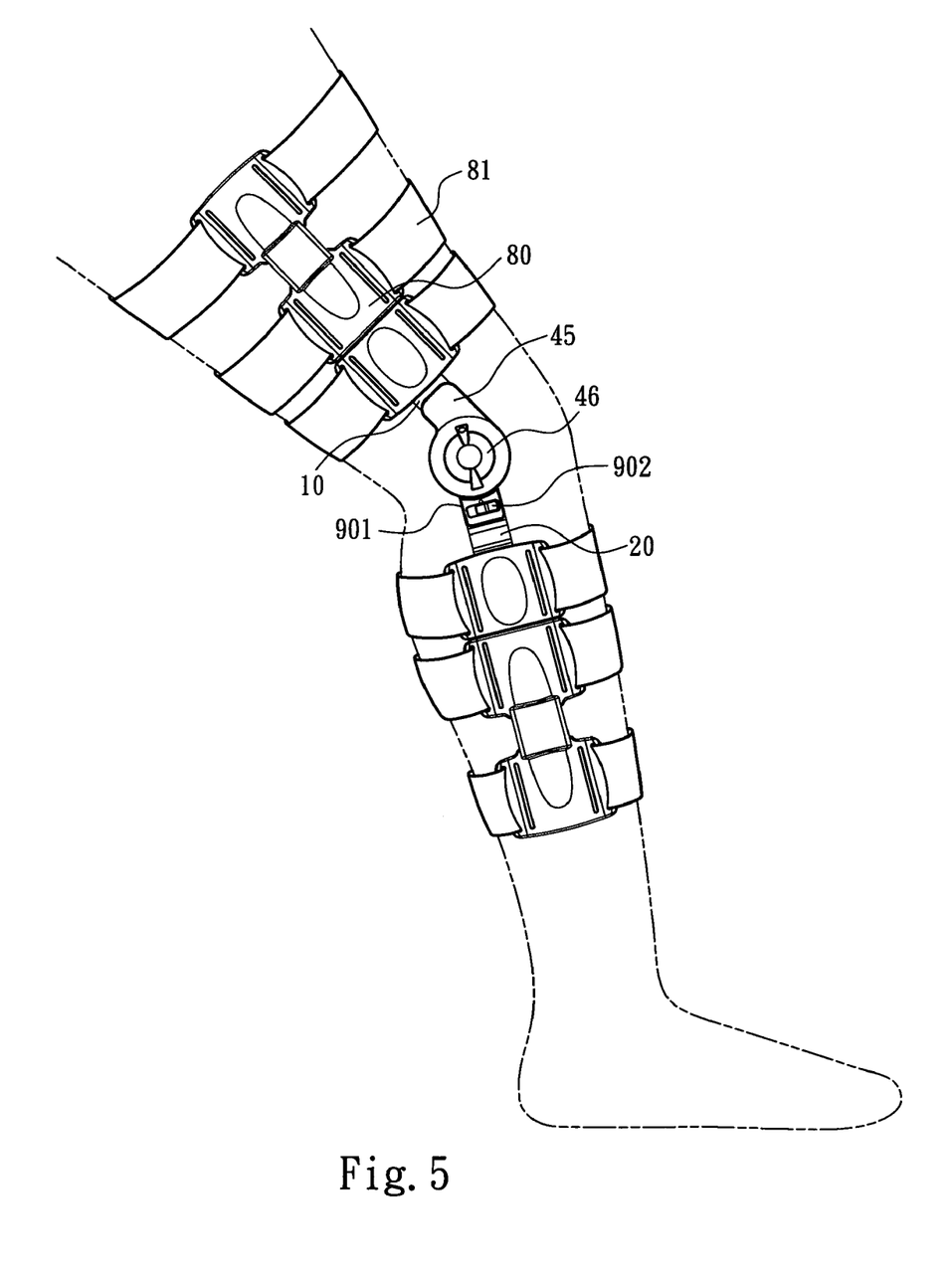
FIG. 5 is a diagram schematically showing one application of the present invention.
Figures 6, 7A:
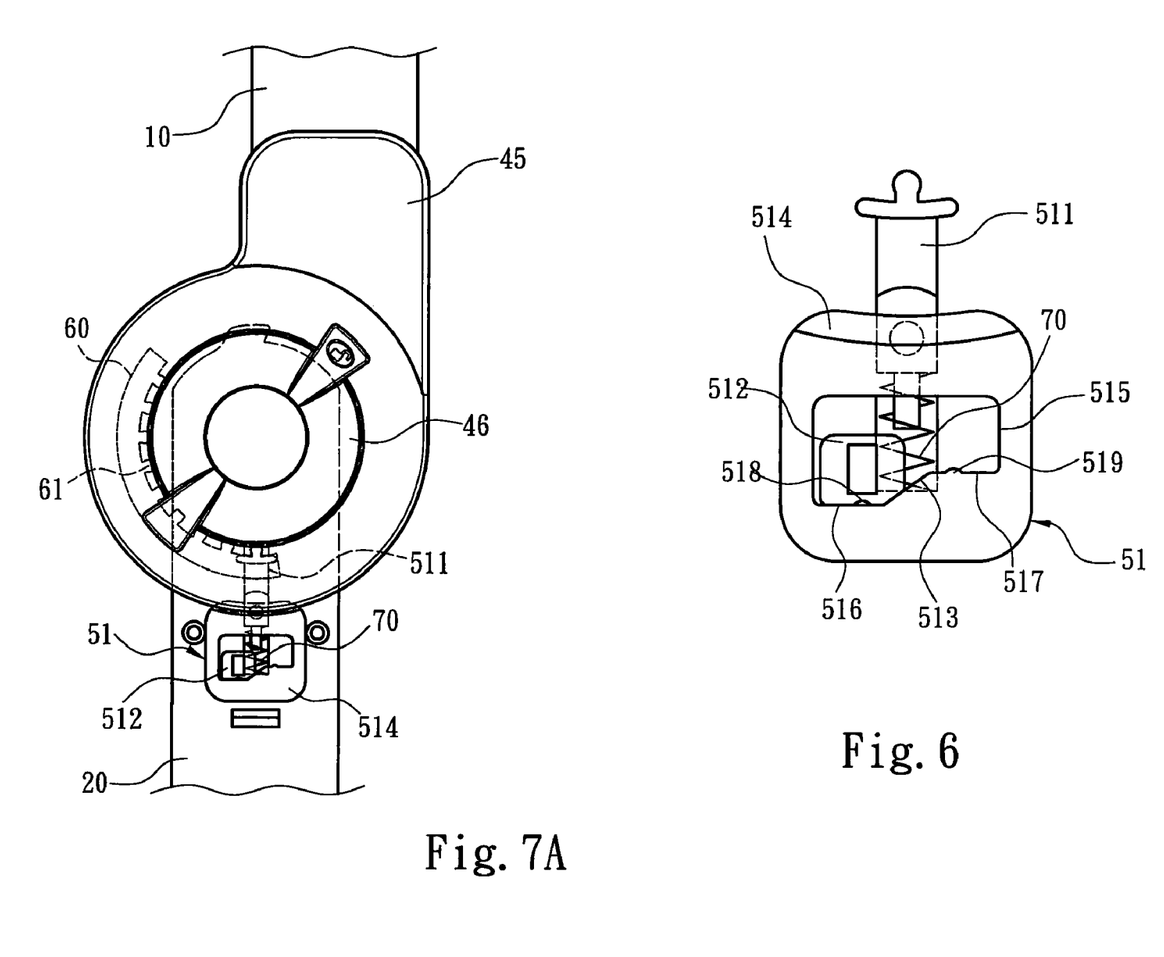
FIG. 6 is a top view of a positioning member of a joint brace adjustable device according to the present invention.
FIGS. 7A-7D are diagrams schematically showing the operation of a positioning member of a joint brace adjustable device according to the present invention.
Figure 7B:
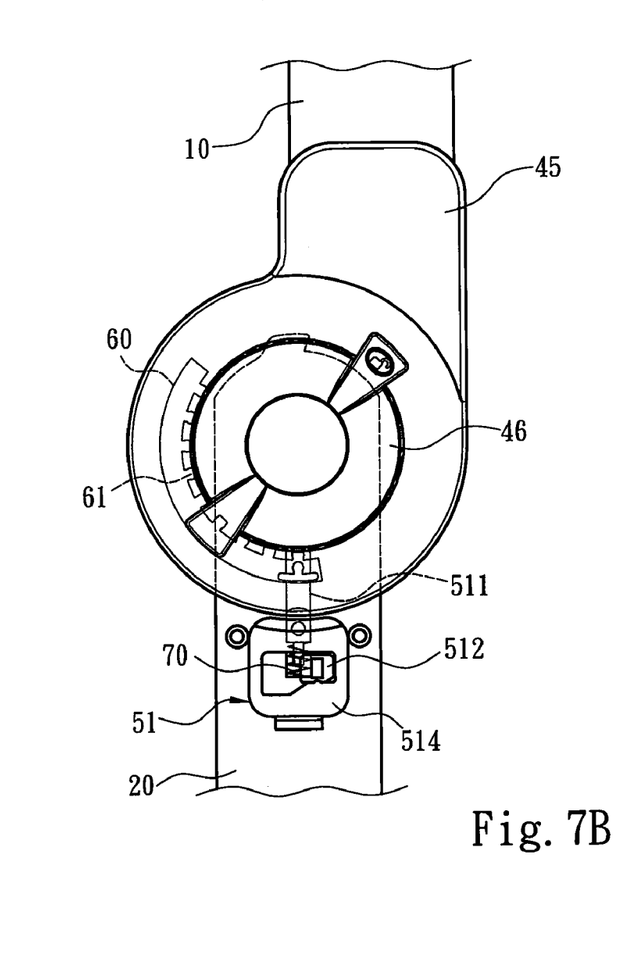
Figure 7C:
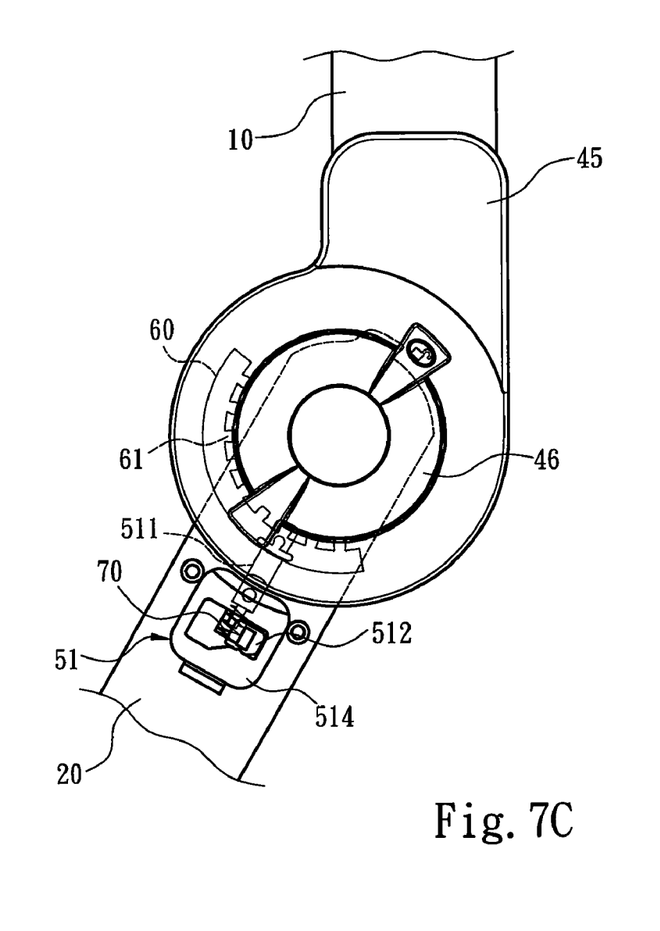
Figure 7D:
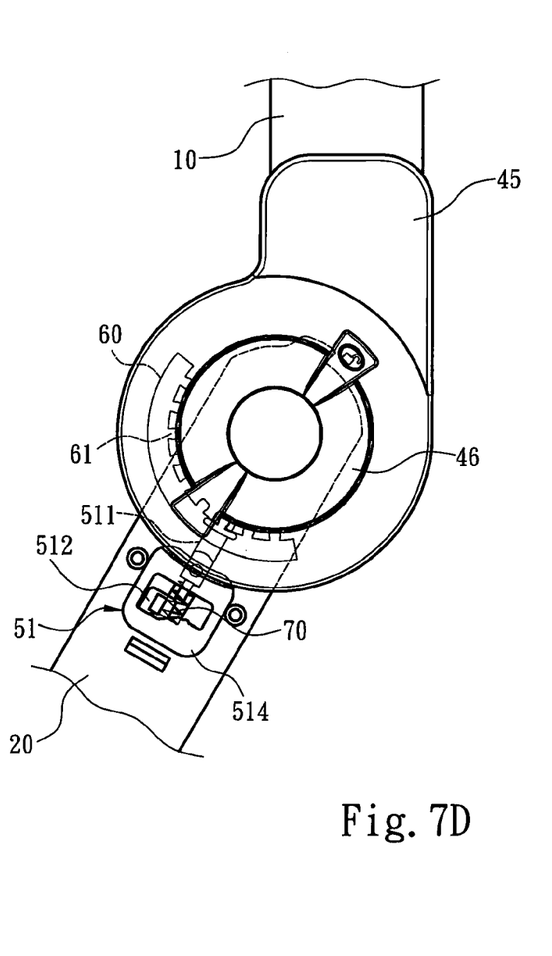
Figure 8A:
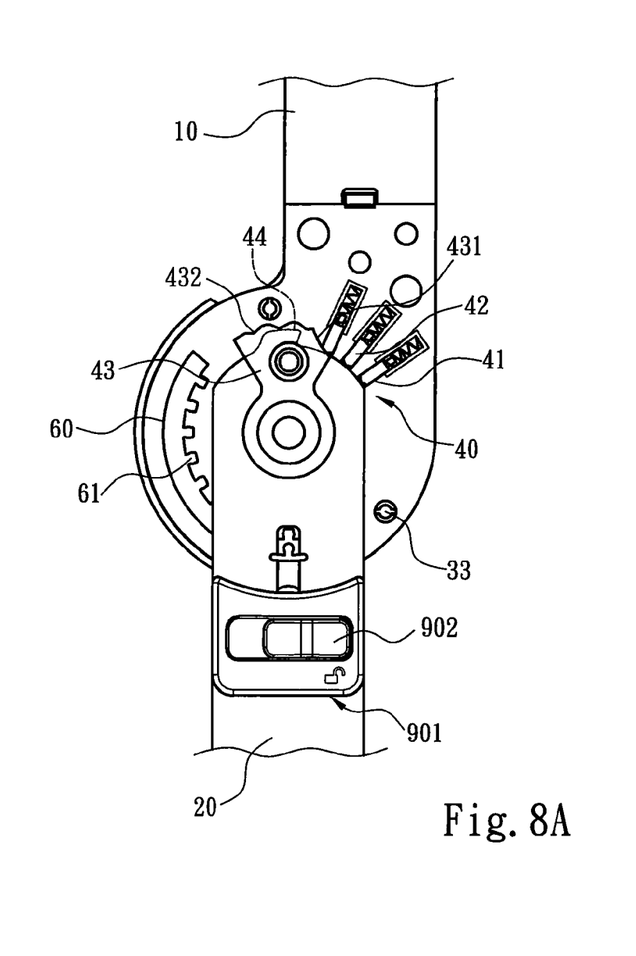
FIGS. 8A-8E are diagrams schematically showing the operation of a motion-limit member of a joint brace adjustable device according to the present invention.
Figure 8B:
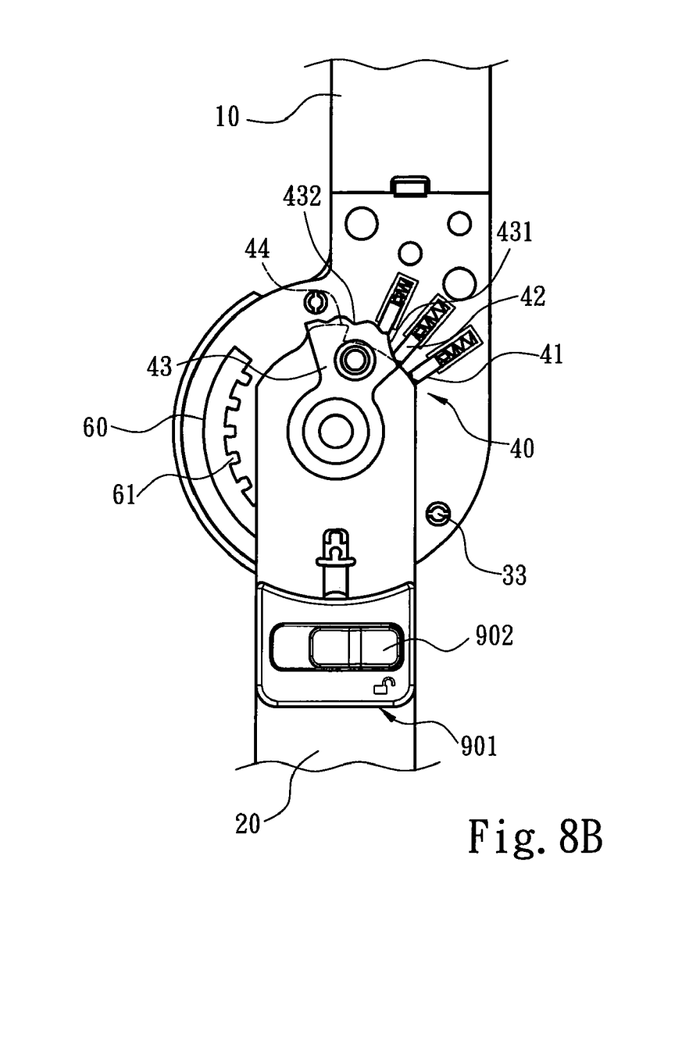
Figure 8C:
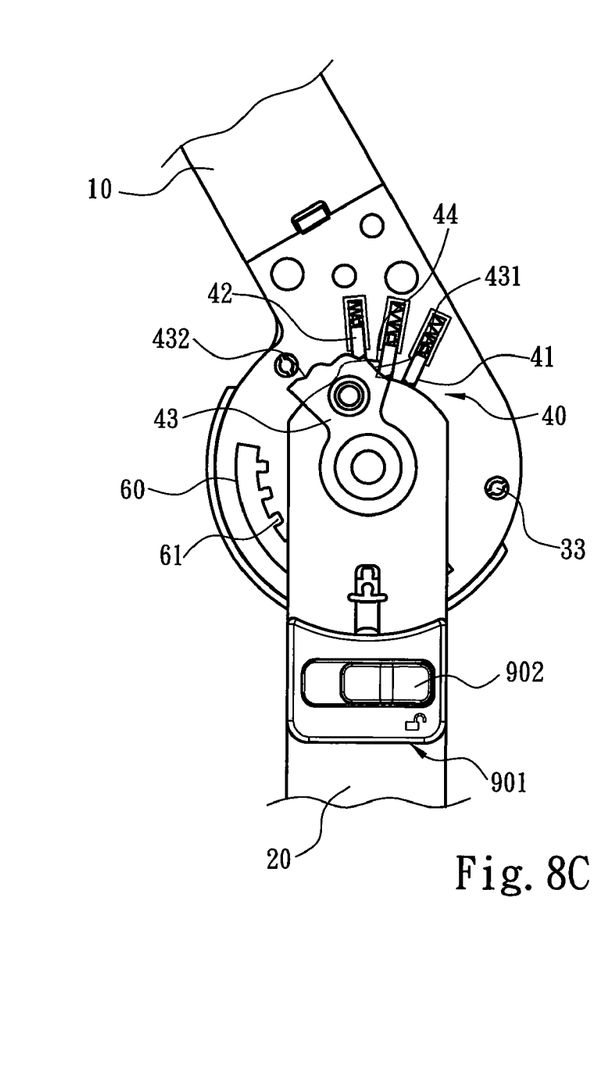
Figure 8D:
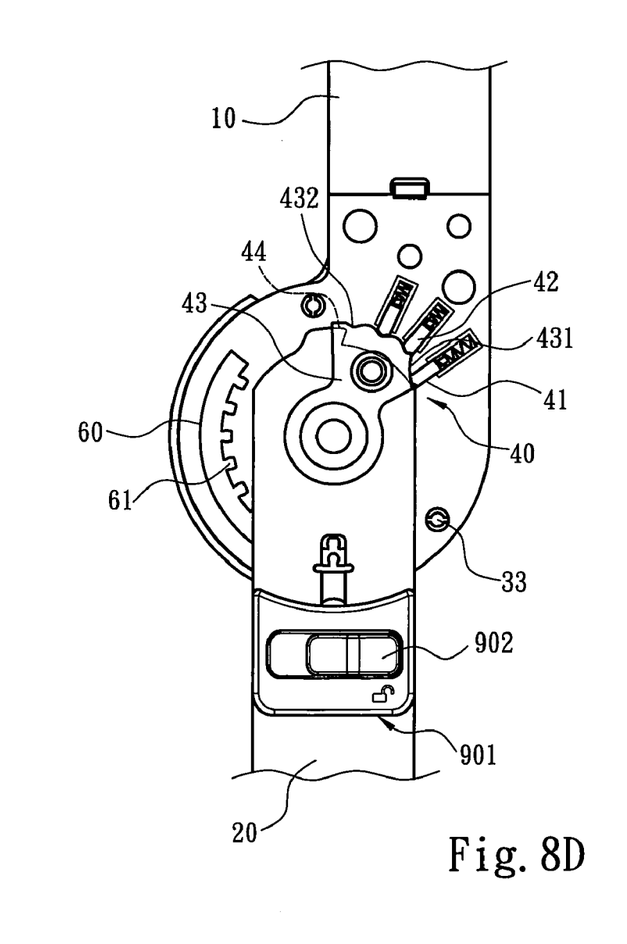
Figure 8E:
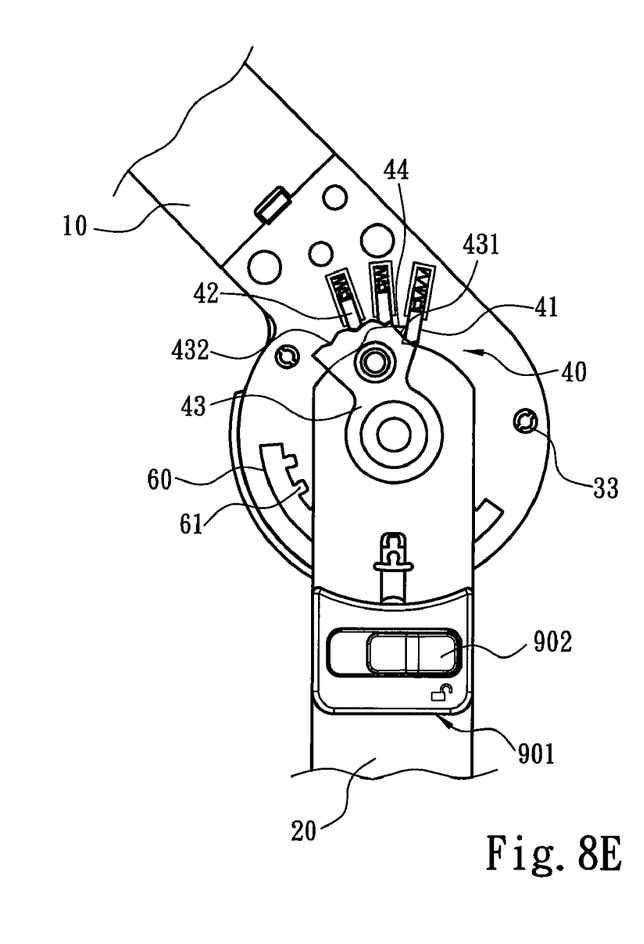

The present invention may be fixed to around the wound area. Refer to FIG. 5, wherein a plurality of fixing plates 80 are arranged on the first and second braces 10 and 20, and a plurality of belt members 81 is inserted through the fixing plates 80 to fix the present invention around the wound area.

Here is described the application of the positioning member 51 is used to position the pivotal disc 30. Suppose that the motion-limit member 40 is unlocked. Switching the switch knob 512 actuates the positioning rod 511, and one end of the positioning rod 511 engages with or departs from the positioning notch 61, wherein the direction of the displacement of the switch knob 512 is parallel to the direction of the displacement of the positioning rod 511. Refer to FIG. 6 and FIGS. 7A-7D. Alternatively, the direction of the displacement of the switch knob 512 is vertical to the direction of the displacement of the positioning rod 511. The positioning member 51 has an elastic element 70 pressing the positioning rod 511 against the positioning notch 61, and an actuation block 514 with one end thereof connected with the positioning rod 511, and the other end thereof having a strip-like position-shifting hole 515 vertical to the positioning rod 511. One side of the position-shifting hole 515 is wider than the opposite side thereof. One edge of the position-shifting hole 515 is near the pivotal disc 30 and straight; the other edge of the position-shifting hole 515 is far away from the pivotal disc 30 has a wide portion 516 and a narrow portion 517. The switch knob 512 is arranged inside the position-shifting hole 515 and contacts the wide portion 516 and the narrow portion 517. The junction of the wide and narrow portions 516 and 517 has an incline 513, and the switch knob 512 also has an incline 513 corresponding to the inclined junction. The switch knob 512, and the wide and narrow portions 516 and 517 respectively have corresponding convex points 519 and concave points 518. Below is described the operation of the positioning member 51. When the first and second braces 10 and 20 is fixed to have a specified angle, the switch knob 512 contacts the wide portion 516, and the elastic element 70 presses the positioning rod 511 against the positioning notch 61. Thus, one end of the positioning rod 511 engages with the positioning notch 61. When the user intends to unlock the fixed-angle state, he moves the switch knob 512 from the wide portion 516 through the incline 513 to the narrow portion 517. Thus, the actuation block 514 backs away, and the positioning rod 511 is also drawn back. Thereby, one end of the positioning rod 511 departs from the positioning notch 61, and the fixed-angle state is unlocked. Next, the first and second braces 10 and 20 are moved to have an intended angle. When the user intends to lock the angle, he moves the switch knob 512 from the narrow portion 517 through the incline 513 to the wide portion 516. Thus, the actuation block 514 is released by the elastic element 70 and presses the positioning rod 511 against the positioning notch 61, and one end of the positioning rod 511 engages with the positioning notch 61. Then, the angle of the first and second braces 10 and 20 is locked. The concave point 518 and convex points 519 are used to fix the switch knob 512 securely to the wide portion 516 and the narrow portion 517. Hereinbefore has been described the operation of the positioning member 51. Additionally, the positioning slot 60 has an arc shape to match the shape of the pivotal disc 30.

Refer to FIGS. 8A-8E for the operation of the motion-limit member 40. Suppose that the positioning member 51 has unlocked the fixed-angle state. The range-adjust member 43 has an incline 431, and the slide block 42 also has an incline 431 corresponding to the incline 431 of the range-adjust member 43. The range-adjust member 43 has contact grooves 432 in the points where the slide block 42 presses against the range-adjust member 43. The contact grooves 432 make the range-adjust member 43 able to clutch the slide block 42 stepwise. In the embodiment shown in the drawings, the discrete-clutch function of the contact grooves 432 is realized by the waved shape having several arcs. However, the contact grooves 432 are not limited to the waved shape having several arcs in the present invention. The contact grooves 432 may also be a shape having several triangles or notches, or any shape able to clutch the slide block 42 stepwise. Initially, when the motion-limit member 40 is set to have a minimum angle (i.e. the first and second braces 10 and 20 have a minimum moveable range), the slide block 42 is pressed toward the axis of the pivotal disc 30. At this time, only a small-angle movement of the block portion 44 is sufficient to enable the slide block 42 to retard the block portion 44. At this time, the movement of the first and second braces 10 and 20 is stopped when the second brace 20 contact the limit element 33. When the user intends to increase the movement range of the first and second braces 10 and 20, he rotates the range-adjust member 43. At this time, the range-adjust member 43 presses against the slide block 42 via the incline 431 to one contact groove 432. Thus, the block portion 44 is no more blocked by the initial slide block 42 but limited by the next slide block 42. Then, the movement range of the first and second braces 10 and 20 is enlarged. The more the range-adjust member 43 the slide blocks 42 press, the larger the movement range the first and second braces 10 and 20 have. When all the slide blocks 42 press against the range-adjust member 43, the block portion 44 is no more blocked by any slide block 42. At this time, the movement range of the first and second braces 10 and 20 begins from the limit element 33 contacting one lateral edge of the second brace 20 to the other limit element 33 contacting the other lateral edge of the second brace 20. In other words, the motion-limit member 40 is in an unlocked state. In the present invention, the number of the slide blocks 42 and the position-fix slots 41 varies according to the practical requirement.

In the present invention, a casing 45 is used to encase the pivotal disc 30. The casing 45 has an adjustable cover 46 and a through-hole 47. The adjustable cover 46 passes through the through-hole 47 to connect with and actuate the range-adjust member 43. According to the installation location of the slide blocks 42 and the position-fix slots 41, marks are formed on the casing 45 to indicate the angles of the movement ranges and convenience the operation. Additionally, the positioning member 51 has a switch-knob frame 901 and a switch-knob cover 902. The switch-knob frame 901 has a through-hole 92. The switch-knob cover 902 passes through the through-hole 92 to connect with and actuate the switch knob 512. A mark is formed on the switch-knob frame 901 to indicate the unlock position and convenience the operation.

The embodiments described above are only to exemplify the present invention but not to limit the scope of the present invention. Any modification or variation according to the spirit of the present invention is to be also included within the scope of the present invention, which is based on the claims stated below.

What is claimed is:

1. A joint brace adjustable device, comprising a first brace, a second brace, and a pivotal disc fixedly coupled to said first brace and pivotally coupled to said second brace, wherein said pivotal disc has a motion-limit member and a positioning slot, and said positioning slot has a plurality of positioning notches, and wherein said second brace has a positioning member used to fix an angle of said first brace and said second brace, and characterized in that said motion-limit member includes a range-adjust member rotatable with respect to said pivotal disc, a plurality of position-fix slots formed on said pivotal disc, a slide block arranged inside said position-fix slot and pressed by said range-adjust member to move toward the circumference of said pivotal disc, an elastic element arranged on one end of said slide block and pushes said slide block toward an axis of said pivotal disc, and a block portion formed on one end of said second brace, and that said positioning member has a positioning rod with one end of thereof matching the shape of said positioning notch and a switch knob coupled to said positioning rod, and that said pivotal disc has an upper disc and a lower disc; said first brace is fixedly coupled to between said upper disc and said lower disc; said second brace are pivotally coupled to between said upper disc and said lower disc, and that said pivotal disc has two limit elements respectively blocking two lateral edges of said second brace;

wherein contact surfaces of said range-adjust member and said slide block respectively have inclines; said range-adjust member has contact grooves in points where said range-adjust member presses against said slide block, and said contact grooves correspond to said slide block.

2. The joint brace adjustable device according to claim 1, wherein a casing is used to encase said pivotal disc; said casing has an adjustable cover and a through-hole; said adjustable cover passes through said through-hole to connect with and actuate said range-adjust member.

3. The joint brace adjustable device according to claim 2, wherein said positioning member has an elastic element pressing said positioning rod against said positioning notch and an actuation block with one end thereof connected with said positioning rod and the other end thereof having a strip-like position-shifting hole vertical to said positioning rod; one side of said position-shifting hole is wider than the opposite side thereof; one edge of said position-shifting hole is near said pivotal disc and straight; the other edge of said position-shifting hole is far away from said pivotal disc and has a wide portion and a narrow portion; said switch knob is arranged inside said position-shifting hole and contacts said wide portion and said narrow portion; a junction of said wide portion and said narrow portion has an incline, and said switch knob also has an incline in a location where said switch knob contacts said junction; said switch knob, and said wide portion and said narrow portion respectively have corresponding convex points and concave points.

4. The joint brace adjustable device according to claim 3, wherein said positioning member has a switch-knob frame and a switch-knob cover; said switch-knob frame has a through-hole; said switch-knob cover passes through said through-hole to connect with and actuate said switch knob.

5. The joint brace adjustable device according to claim 1, wherein a plurality of fixing plates are arranged on said first brace and said second brace.

* * * * *